(12) United States Patent
Yang et al.

(10) Patent No.: US 7,943,089 B2
(45) Date of Patent: May 17, 2011

(54) LAMINATED ASSAY DEVICES

(75) Inventors: Kaiyuan Yang, Cumming, GA (US);
Xuedong Song, Roswell, GA (US);
Rosann Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 367 days.

(21) Appl. No.: 10/741,434

(22) Filed: Dec. 19, 2003

(65) Prior Publication Data

US 2005/0136529 A1   Jun. 23, 2005

(51) Int. Cl.
*G01N 27/00* (2006.01)
(52) U.S. Cl. ... 422/82.01; 422/50; 422/68.1; 435/283.1; 435/287.2; 435/7.1; 436/518; 436/524
(58) Field of Classification Search ............. 422/50, 422/61, 68.1, 82.01, 82.03; 435/4, 7.1, 7.9, 435/7.93, 7.94, 7.95, 7.4, 174, 283.1, 285.2, 435/287.1, 287.2; 436/501, 518, 524, 525
See application file for complete search history.

(56) References Cited

U.S. PATENT DOCUMENTS

| | | | |
|---|---|---|---|
| 1,366,241 A | 1/1921 | Burch | |
| 3,700,623 A | 10/1972 | Keim | |
| 3,772,076 A | 11/1973 | Keim | |
| 4,094,647 A | 6/1978 | Deutsch et al. | |
| 4,110,529 A | 8/1978 | Stoy | |
| 4,168,146 A | 9/1979 | Grubb et al. | |
| RE30,267 E | 5/1980 | Bruschi | |
| 4,210,723 A | 7/1980 | Dorman et al. | |
| 4,275,149 A | 6/1981 | Litman et al. | |
| 4,280,815 A * | 7/1981 | Oberhardt et al. | ............ 436/518 |
| 4,312,228 A | 1/1982 | Wohltjen | |
| 4,363,874 A | 12/1982 | Greenquist | |
| 4,366,241 A | 12/1982 | Tom et al. | |
| 4,374,925 A | 2/1983 | Litman et al. | |
| 4,385,126 A | 5/1983 | Chen et al. | |
| 4,426,451 A | 1/1984 | Columbus | |
| 4,427,836 A | 1/1984 | Kowalski et al. | |

(Continued)

FOREIGN PATENT DOCUMENTS

EP   0073593 A1   3/1983

(Continued)

OTHER PUBLICATIONS

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

(Continued)

*Primary Examiner* — Melanie J Yu
(74) *Attorney, Agent, or Firm* — Dority & Manning, P.A.

(57) ABSTRACT

An electrochemical-based assay device capable of detecting the presence or quantity of an analyte of interest that is provided. The device contains two or more substrates, one containing a detection working electrode and another containing an auxiliary electrode, such as a counter/reference electrode (s). The substrates are positioned in a face-to-face relationship so that the electrodes are adjacent to each other during performance of the assay. Besides the electrodes, any of a variety of other components may also be employed in the assay device.

18 Claims, 6 Drawing Sheets

U.S. PATENT DOCUMENTS

| | | |
|---|---|---|
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,657 A | 8/1985 | Keim |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,586,695 A | 5/1986 | Miller |
| 4,595,661 A | 6/1986 | Cragle et al. |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A | 10/1987 | Campbell et al. |
| 4,722,889 A | 2/1988 | Lee et al. |
| 4,727,019 A | 2/1988 | Valkirs et al. |
| 4,731,337 A | 3/1988 | Luotola et al. |
| 4,743,542 A | 5/1988 | Graham, Jr. et al. |
| 4,776,944 A | 10/1988 | Janata et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,877,586 A | 10/1989 | Devaney, Jr. et al. |
| 4,877,747 A | 10/1989 | Stewart |
| 4,895,017 A | 1/1990 | Pyke et al. |
| 4,916,056 A | 4/1990 | Brown, III et al. |
| 4,917,503 A | 4/1990 | Bhattacharjee |
| 4,940,734 A | 7/1990 | Ley et al. |
| 4,963,498 A | 10/1990 | Hillman et al. |
| 4,973,670 A | 11/1990 | McDonald et al. |
| 4,992,385 A | 2/1991 | Godfrey |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,075,077 A | 12/1991 | Durley, III et al. |
| 5,076,094 A | 12/1991 | Frye et al. |
| 5,096,671 A | 3/1992 | Kane et al. |
| 5,114,676 A | 5/1992 | Leiner et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,141,868 A | 8/1992 | Shanks et al. |
| 5,143,854 A | 9/1992 | Pirrung et al. |
| 5,145,784 A | 9/1992 | Cox et al. |
| 5,152,758 A | 10/1992 | Kaetsu et al. |
| 5,156,953 A | 10/1992 | Litman et al. |
| 5,179,288 A | 1/1993 | Miffitt et al. |
| 5,182,135 A | 1/1993 | Giesecke et al. |
| 5,196,350 A | 3/1993 | Backman et al. |
| 5,200,084 A | 4/1993 | Liberti et al. |
| 5,208,535 A | 5/1993 | Nakayama et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |
| 5,482,867 A | 1/1996 | Barrett et al. |
| 5,484,867 A | 1/1996 | Lichtenham et al. |
| 5,489,678 A | 2/1996 | Fodor et al. |
| 5,489,988 A | 2/1996 | Ackley et al. |
| 5,492,840 A | 2/1996 | Malmqvist et al. |
| 5,500,350 A | 3/1996 | Baker et al. |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,514,559 A | 5/1996 | Markert-Hahn et al. |
| 5,514,785 A | 5/1996 | Van Ness et al. |
| 5,516,635 A | 5/1996 | Ekins et al. |
| 5,518,689 A | 5/1996 | Dosmann et al. |
| 5,518,883 A | 5/1996 | Soini |
| 5,527,711 A | 6/1996 | Tom-Moy et al. |
| 5,531,878 A * | 7/1996 | Vadgama et al. ............ 205/778 |
| 5,534,132 A | 7/1996 | Vreeke et al. |
| 5,554,539 A | 9/1996 | Chadney et al. |
| 5,554,541 A | 9/1996 | Malmqvist et al. |
| 5,569,608 A | 10/1996 | Sommer |
| 5,571,684 A | 11/1996 | Lawrence et al. |
| 5,573,909 A | 11/1996 | Singer et al. |
| 5,585,279 A | 12/1996 | Davidson |
| 5,589,401 A | 12/1996 | Hansen et al. |
| 5,591,581 A | 1/1997 | Massey et al. |
| 5,596,414 A | 1/1997 | Tyler |
| 5,599,668 A | 2/1997 | Stimpson et al. |
| 5,618,888 A | 4/1997 | Choi et al. |
| 5,620,850 A | 4/1997 | Bamdad et al. |
| 5,637,509 A | 6/1997 | Hemmilä et al. |
| 5,645,709 A * | 7/1997 | Birch et al. ................. 205/775 |
| 5,647,994 A | 7/1997 | Tuunanen et al. |
| 5,658,443 A | 8/1997 | Yamamoto et al. |
| 5,663,213 A | 9/1997 | Jones et al. |
| 5,670,381 A | 9/1997 | Jou et al. |
| 5,672,256 A | 9/1997 | Yee |
| 5,700,636 A | 12/1997 | Sheiness et al. |
| 5,726,064 A | 3/1998 | Robinson et al. |
| 5,731,147 A | 3/1998 | Bard et al. |
| 5,736,188 A | 4/1998 | Alcock et al. |
| 5,753,517 A | 5/1998 | Brooks et al. |
| 5,759,364 A * | 6/1998 | Charlton et al. ......... 204/403.14 |
| 5,770,416 A | 6/1998 | Lihme et al. |
| 5,770,439 A * | 6/1998 | Biliteweski et al. ......... 435/287.1 |
| 5,780,308 A | 7/1998 | Ching et al. |
| 5,795,470 A | 8/1998 | Wang et al. |
| 5,795,543 A | 8/1998 | Poto et al. |
| 5,798,273 A | 8/1998 | Shuler et al. |
| 5,811,526 A | 9/1998 | Davidson |

| | | |
|---|---|---|
| 5,827,748 A | 10/1998 | Golden |
| 5,834,226 A | 11/1998 | Maupin |
| 5,837,429 A | 11/1998 | Nohr et al. |
| 5,837,546 A | 11/1998 | Allen et al. |
| 5,843,692 A | 12/1998 | Phillips et al. |
| 5,852,229 A | 12/1998 | Josse et al. |
| 5,876,944 A | 3/1999 | Kuo |
| 5,885,527 A | 3/1999 | Buechler |
| 5,906,921 A | 5/1999 | Ikeda et al. |
| 5,910,286 A | 6/1999 | Lipskier |
| 5,910,447 A | 6/1999 | Lawrence et al. |
| 5,910,940 A | 6/1999 | Guerra |
| 5,916,156 A * | 6/1999 | Hildenbrand et al. ......... 205/778 |
| 5,922,537 A | 7/1999 | Ewart et al. |
| 5,922,550 A | 7/1999 | Everhart et al. |
| 5,951,492 A | 9/1999 | Douglas et al. |
| 5,954,685 A * | 9/1999 | Tierney ............................ 604/20 |
| 5,962,995 A | 10/1999 | Avnery |
| 5,965,237 A | 10/1999 | Bruin et al. |
| 6,001,239 A * | 12/1999 | Douglas et al. ................ 205/778 |
| 6,004,530 A | 12/1999 | Sagner et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,030,840 A | 2/2000 | Mullinax et al. |
| 6,033,574 A | 3/2000 | Siddiqi |
| 6,048,623 A | 4/2000 | Everhart et al. |
| 6,060,256 A | 5/2000 | Everhart et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,103,537 A | 8/2000 | Ullman et al. |
| 6,117,090 A | 9/2000 | Caillouette |
| 6,136,549 A | 10/2000 | Feistel |
| 6,136,611 A | 10/2000 | Saaski et al. |
| 6,139,961 A | 10/2000 | Blankenship et al. |
| 6,151,110 A | 11/2000 | Markart |
| 6,156,173 A * | 12/2000 | Gotoh et al. ............. 204/403.04 |
| 6,165,798 A | 12/2000 | Brooks |
| 6,171,780 B1 | 1/2001 | Pham et al. |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,183,972 B1 | 2/2001 | Kuo et al. |
| 6,184,042 B1 | 2/2001 | Neumann et al. |
| 6,194,220 B1 | 2/2001 | Malick et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,235,471 B1 | 5/2001 | Knapp et al. |
| 6,235,491 B1 | 5/2001 | Connolly |
| 6,241,863 B1 | 6/2001 | Monbouquette |
| 6,242,268 B1 | 6/2001 | Wieder et al. |
| 6,255,066 B1 | 7/2001 | Louderback |
| 6,261,779 B1 | 7/2001 | Barbera-Guillem et al. |
| 6,268,222 B1 | 7/2001 | Chandler et al. |
| 6,270,637 B1 | 8/2001 | Crismore et al. |
| 6,271,040 B1 | 8/2001 | Buechler |
| 6,281,006 B1 | 8/2001 | Heller et al. |
| 6,284,472 B1 | 9/2001 | Wei et al. |
| 6,287,783 B1 | 9/2001 | Maynard et al. |
| 6,287,871 B1 | 9/2001 | Herron et al. |
| 6,294,392 B1 | 9/2001 | Kuhr et al. |
| 6,303,288 B1 | 10/2001 | Furcht et al. |
| 6,306,665 B1 | 10/2001 | Buck et al. |
| D450,854 S | 11/2001 | Lipman et al. |
| 6,331,438 B1 | 12/2001 | Aylott et al. |
| 6,342,347 B1 * | 1/2002 | Bauer ................................ 435/4 |
| 6,348,186 B1 | 2/2002 | Sutton et al. |
| 6,362,011 B1 | 3/2002 | Massey et al. |
| 6,368,873 B1 | 4/2002 | Chang et al. |
| 6,368,875 B1 | 4/2002 | Geisberg |
| 6,387,707 B1 | 5/2002 | Seul et al. |
| 6,391,558 B1 | 5/2002 | Henkens et al. |
| 6,399,295 B1 | 6/2002 | Kaylor et al. |
| 6,399,397 B1 | 6/2002 | Zarling et al. |
| 6,407,492 B1 | 6/2002 | Avnery et al. |
| 6,411,439 B2 | 6/2002 | Nishikawa |
| 6,413,410 B1 | 7/2002 | Hodges et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,451,607 B1 | 9/2002 | Lawrence et al. |
| 6,455,861 B1 | 9/2002 | Hoyt |
| 6,461,496 B1 | 10/2002 | Feldman et al. |
| 6,468,741 B1 | 10/2002 | Massey et al. |
| 6,472,226 B1 | 10/2002 | Barradine et al. |
| 6,479,146 B1 | 11/2002 | Caruso et al. |
| 6,498,497 B1 * | 12/2002 | Chow et al. .................... 324/601 |
| 6,509,085 B1 | 1/2003 | Kennedy |
| 6,509,196 B1 | 1/2003 | Brooks et al. |
| 6,511,814 B1 | 1/2003 | Carpenter |
| 6,518,168 B1 | 2/2003 | Clem et al. |
| 6,551,495 B1 | 4/2003 | Porter et al. |
| 6,556,299 B1 | 4/2003 | Rushbrooke et al. |
| 6,559,474 B1 | 5/2003 | Craighead et al. |
| 6,566,508 B2 | 5/2003 | Bentsen et al. |
| 6,573,040 B2 | 6/2003 | Everhart et al. |
| 6,579,673 B2 | 6/2003 | McGrath et al. |
| 6,582,930 B1 | 6/2003 | Ponomarev et al. |
| 6,585,939 B1 | 7/2003 | Dapprich |
| 6,607,922 B2 | 8/2003 | LaBorde |
| 6,613,583 B1 | 9/2003 | Richter et al. |
| 6,617,488 B1 | 9/2003 | Springer et al. |
| 6,670,115 B1 | 12/2003 | Zhang |
| 6,720,007 B2 | 4/2004 | Walt et al. |
| 6,758,951 B2 * | 7/2004 | Giaquinta et al. .............. 506/32 |
| 6,787,368 B1 | 9/2004 | Wong et al. |
| 6,815,218 B1 | 11/2004 | Jacobson et al. |
| 2001/0055776 A1 | 12/2001 | Greenwalt |
| 2002/0070128 A1 | 6/2002 | Beckmann |
| 2002/0146754 A1 | 10/2002 | Kitawaki et al. |
| 2002/0164659 A1 | 11/2002 | Rao et al. |
| 2003/0017615 A1 | 1/2003 | Sidwell et al. |
| 2003/0024811 A1 | 2/2003 | Davies et al. |
| 2003/0111357 A1* | 6/2003 | Black ............................ 205/775 |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2003/0157587 A1 | 8/2003 | Gomez et al. |
| 2003/0162236 A1 | 8/2003 | Harris et al. |
| 2003/0178309 A1 | 9/2003 | Huang et al. |
| 2004/0014073 A1 | 1/2004 | Trau et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0106190 A1 * | 6/2004 | Yang et al. .................. 435/287.2 |
| 2004/0115861 A1 | 6/2004 | Wong et al. |

FOREIGN PATENT DOCUMENTS

| | | |
|---|---|---|
| EP | 0420053 A1 | 4/1991 |
| EP | 0437287 B1 | 7/1991 |
| EP | 0469377 A2 | 2/1992 |
| EP | 0617285 A2 | 9/1994 |
| EP | 0617285 A3 | 9/1994 |
| EP | 0703454 A1 | 3/1996 |
| EP | 0462376 B1 | 7/1996 |
| EP | 0724156 A1 | 7/1996 |
| EP | 0745843 A2 | 12/1996 |
| EP | 0745843 A3 | 12/1996 |
| EP | 0859230 A1 | 8/1998 |
| EP | 0898169 B1 | 2/1999 |
| EP | 0711414 B1 | 3/1999 |
| EP | 1221616 A1 | 7/2002 |
| GB | 2273772 A | 6/1994 |
| WO | WO 8804777 A1 | 6/1988 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |

| | | |
|---|---|---|
| WO | WO 9319370 A1 | 9/1993 |
| WO | WO 9413835 A1 | 6/1994 |
| WO | WO 9415193 A1 | 7/1994 |
| WO | WO 9709620 A1 | 3/1997 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0046839 A2 | 8/2000 |
| WO | WO 0046839 A3 | 8/2000 |
| WO | WO 0047983 A1 | 8/2000 |
| WO | WO 0050891 A1 | 8/2000 |
| WO | WO 0078917 A1 | 12/2000 |
| WO | WO 0138873 A2 | 5/2001 |
| WO | WO 0163299 A1 | 8/2001 |
| WO | WO 0198765 A1 | 12/2001 |
| WO | WO 0198785 A2 | 12/2001 |
| WO | WO 03005013 A1 | 1/2003 |
| WO | WO 03080327 A1 | 10/2003 |

OTHER PUBLICATIONS

PCT Search Report and Written Opinion for PCT/US2004/006412, Sep. 28, 2004.

PCT Search Report and Written Opinion for PCT/US2004/006414, Sep. 28, 2004.

Abstract of Japanese Patent No. JP 8062214, Mar. 8, 1996.

Abstract of Article—*Factors influencing the formation of hollow ceramic microspheres by water extraction of colloidal droplets*, J. Mater. Res., vol. 10, No. 1, p. 84, 1996.

Article—*A conductometric biosensor for biosecurity*, Zarini Muhammid-Tahir and Evangelyn C. Alocilja, Biosensors and Bioelectronics 18, 2003, pp. 813-819.

Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.

Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.

Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp, 4247-4249.

Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.

Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.

Article—*Analysis of electrical equivalent circuit of quartz crystal resonator loaded with viscous conductive liquids*, Journal of Electroanalytical Chemistry, vol. 379, 1994, pp. 21-33.

Article—*Application of rod-like polymers with ionophores as Langmuir-Blodgett membranes for Si-based ion sensors*, Sensors and Actuators B, 1992, pp. 211-216.

Article—*Attempts to Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.

Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.

Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.

Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages, 1993, pp. 197-205.

Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—Flow-*Based Microimmunoassay*, Analytical Chemistry, vol. 73, No. 24, Mark A. Hayes, Nolan A. Polson, Allison, N. Phayre, and Antonia A. Garcia, Dec. 15, 2001, pp. 5896-5902.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Hollow latex particles: synthesis and applications*, Charles J. McDonald and Michael J. Devon, Advances in Colloid and Interface Science, Vo. 99, 2002, pp. 181-213.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.

Article—*Molecular Gradients of ω-Substituted Alkanethiols on Gold: Preparation and Characterization*, Bo Liedberg and Pentti Tengvall, Langmuir, vol. 11, No. 10, 1995, pp. 3821-3827.

Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.

Article—*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp. 352-357.

Article—*New Approach to Producing Patterned Biomolecular Assemblies*, Suresh K. Bhatia, James J. Hickman, and Frances S. Ligler, J. Am. Chem. Soc., vol. 114, 1992,pp. 4433-4434.

Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Orientation dependence of surface segregation in a dilute Ni-Au alloy*, W . C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives of ($n^5$-$C_5H_5$)$Mn(CO)_3$*, Doris Kang and Mark S. Wrighton, Langmuir, vol. 7, No. 10, 1991, pp. 2169-2174.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article —*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages, 1993, pp. 129-130.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Quantitative Prediction of Surface Segregation*, M. P. Seah, Journal of Catalysts, vol. 57, 1979, pp. 450-457.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Responsive Gels: Volume Transitions I*, M. Ilayský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages, 1993.

Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films for Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

Article—*Sensing liquid properties with thickness-shear mode resonators*, S. J. Martin, G. C. Frye, and K.O. Wessendorf, Sensors and Actuators A, vol. 44, 1994, pp. 209-218.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Stimuli-Responsive Poly(N-isopropylacrylamide) Photo- and Chemical-Induced Phase Transitions*, Advances in Polymer Science, pp. 50-65.

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article—*Volume Phase Transition of N-Alkylacrylamide Gels*, S. Saito, M. Konno, and H. Inomata, Advances in Polymer Science, vol. 109, 1992, pp. 207-232.

Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.

Working With FluoSpheres® Fluorescent Microspheres, Properties and Modifications, Product Information from Molecular Probes, Mar. 9, 2001, pp. 1-5.

PCT Search Report for PCT/US03/21520, Dec. 15, 2003.

PCT Search Report for PCT/US02/37653, Apr. 7, 2004.

PCT Search Report for PCT/US03/28628, Mar. 18, 2004.

PCT Search Report for PCT/US03/34543, Apr. 6, 2004.

PCT Search Report for PCT/US03/34544, Apr. 20, 2004.

Abstract of DE10024145A1, Nov. 22, 2001.

Article—*Solid Substrate Phosphorescent Immunoassay Based on Bioconjugated*, 2001 pp. 1627-1637.

*Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

PCT Search Report and Written Opinion for PCT/US2004/013180, Aug. 17, 2004.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.

Article—*Inert Phosphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, No. 6, 2001, pp. 883-889.

Article—*Intelligent Gels*, Yoshihito Osada and Simon B. Ross-Murphy, Scientific American, May 1993, pp. 82-87.

Article—*Latex Immunoassays*, Leigh B. Bangs, Journal of Clinical Immunoassay, vol. 13, No. 3, 1990, pp. 127-131.

Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Microfabrication by Microcontact Printing of Self-Assembled Monolyaers*, James L. Wilbur, Armit Kumar, Enoch Kim, and George M. Whitesides, Advanced Materials, vol. 6, No. 7/8, 1994, pp. 600-604.

* cited by examiner

LAMINATED ASSAY DEVICES

BACKGROUND OF THE INVENTION

Various analytical procedures and devices are commonly employed in assays to determine the presence and/or absence of analytes in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample. There are several well-known techniques for detecting the presence of an analyte.

One such technique is described in WO 01/38873 to Zhang. Zhang describes flow-through electrochemical biosensors designed to detect the presence of an analyte. FIG. 2 of Zhang, for instance, illustrates a sensor assembly 5 that includes an absorbent pad 18, a wicking mesh 22, and a conjugate pad 20 that overlay an application area 14' and a detection area 16'. The wicking mesh 22 functions as a carrier to deliver the fluid sample through capillary action to the detection area 16' where the analyte will become immobilized on the electrode surface. In Example 4 of Zhang, various materials of different pore sizes (ranging from 0.63 to 100 microns) were tested to determine the time for a buffer solution to flow 4 centimeters along the membrane. The times ranged from 40 seconds to 3 minutes, 45 seconds. Zhang indicates that any of the membranes tested could be used to provide a rapid test.

Unfortunately, conventional flow-through electrochemical biosensors, such as described above, possess various problems. For instance, traditional flow-through assay devices require a large sample volume because of the presence of a large sampling pad, wicking pad, and porous membrane. Moreover, the contact of the sample with the working electrode surface is not always sufficient because a large portion of the sample does not flow through the electrode surface, rather it flows through the membrane itself and bypasses the working electrode. Furthermore, the positioning of two or more electrodes close to each other poses a challenge for the surface treatment of the working electrode. In particular, such biosensors often exhibit substantial background interference due to contamination of the counter/reference electrode(s) resulting from surface treatment of the working electrode. As such, a need still exits for an improved flow-through, electrochemical assay device.

SUMMARY OF THE INVENTION

In accordance with one embodiment of the present invention, an assay device is disclosed for detecting the presence or quantity of an analyte residing in a test sample. The assay device comprises a first substrate defining a first surface on which is disposed a detection working electrode. The assay device further comprises a second substrate defining a second surface on which is disposed an auxiliary electrode (e.g., counter electrode, reference electrode, or combinations thereof). The first substrate and the second substrate are at least partially laminated together so that the first surface faces the second surface, wherein the detection working electrode is capable of generating a measurable detection current that is proportional to the amount of the analyte within the test sample.

In accordance with another embodiment of the present invention, an assay device for detecting the presence or quantity of an analyte residing in a test sample is disclosed. The assay device comprises a first substrate defining a first surface on which is disposed a detection working electrode treated with an affinity reagent. The assay device further comprises a second substrate defining a second surface on which is disposed a counter electrode, a reference electrode, or combinations thereof. The first substrate and the second substrate are at least partially laminated together so that the first surface faces the second surface, wherein the detection working electrode is capable of generating a measurable detection current that is proportional to the amount of the analyte within the test sample.

In accordance with still another embodiment of the present invention, a method for forming an assay device is disclosed. The method comprises treating a detection working electrode disposed on a first surface of a first substrate with an affinity reagent. Thereafter, the first substrate is at least partially laminated to a second substrate. The second substrate defines a second surface on which is disposed an auxiliary electrode, wherein the first surface of the first substrate faces the second surface of the second substrate.

In accordance with yet another embodiment of the present invention, a method for detecting the presence or quantity of an analyte residing in a test sample is disclosed. The method comprises treating a detection working electrode disposed on a first surface of a first substrate with an affinity reagent. Thereafter, the first substrate is at least partially laminated to a second substrate, the second substrate defining a second surface on which is disposed an auxiliary electrode. The first surface of the first substrate faces the second surface of the second substrate. A test sample is allowed to contact the detection working electrode. A potential difference is applied between the detection working electrode and the auxiliary electrode to generate a detection current. In some embodiments, the method may further comprise applying a potential difference between a calibration working electrode disposed on the first surface of the first substrate and the auxiliary electrode to generate a calibration current. The calibration current may be used to calibrate the detection current.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
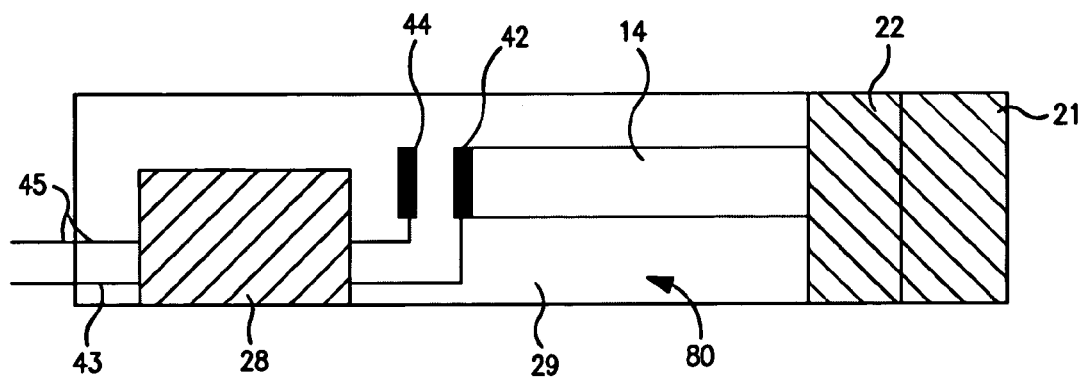
FIG. 1 is a schematic illustration of a substrate containing working electrodes for use in one embodiment of an assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

As used herein, the term "test sample" generally refers to a material suspected of containing the analyte. The test sample may, for instance, include materials obtained directly from a source, as well as materials pretreated using techniques, such as, but not limited to, filtration, precipitation, dilution, distillation, mixing, concentration, inactivation of interfering components, the addition of reagents, and so forth. The test sample may be derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. Besides physiological fluids, other liquid samples may be used, such as water, food products, and so forth. In addition, a solid material suspected of containing the analyte may also be used as the test sample.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to an electrochemical-based assay device capable of detecting the presence or quantity of an analyte of interest that is accurate, reliable, and easy-to-use. The device contains two or more substrates, one containing a detection working electrode and another containing an auxiliary electrode, such as a counter/reference electrode(s). The substrates are positioned in a face-to-face relationship so that the electrodes are placed in electrical communication with each other during performance of the assay.

Referring to FIG. 1, for instance, one embodiment of a first substrate 80 that may be used in an assay device of the present invention is illustrated. Although not required, the first substrate 80 may be formed from an insulative material, such as silicon, fused silicon dioxide, silicate glass, alumina, aluminosilicate ceramic, an epoxy, an epoxy composite such as glass fiber reinforced epoxy, polyester, polyimide, polyamide, polycarbonate, etc. A detection working electrode 42 and an optional calibration working electrode 44 are disposed on a surface 29 of the substrate 80. It should be understood that other detection and/or calibration working electrodes may also be utilized. The detection working electrode 42 is typically formed from a thin film of conductive material disposed on the substrate 80. Generally speaking, a variety of conductive materials may be used to form the detection working electrode 42. Suitable materials include, for example, carbon, metals (platinum, palladium, gold, tungsten, titanium, etc.), metal-based compounds (e.g., oxides, chlorides, etc.), metal alloys, conductive polymers, combinations thereof, and so forth. Particular examples of carbon electrodes include glassy carbon, graphite, mesoporous carbon, nanocarbon tubes, fullerenes, etc. Thin films of these materials may be formed by a variety of methods including, for example, sputtering, reactive sputtering, physical vapor deposition, plasma deposition, chemical vapor deposition (CVD), printing, spraying, and other coating methods. For instance, carbon or metal paste based conductive materials are typically formed using screen printing, which either may be done manually or automatically. Likewise, metal-based electrodes are typically formed using standard sputtering or CVD techniques, or by electrochemical plating.

Discrete conductive elements may be deposited to form the detection working electrode 42, for example, using a patterned mask. Alternatively, a continuous conductive film may be applied to the substrate and then the detection working electrode 42 may be patterned from the film. Patterning techniques for thin films of metal and other materials are well known in the art and include photolithographic techniques. An exemplary technique includes depositing the thin film of conductive material and then depositing a layer of a photoresist over the thin film. Typical photoresists are chemicals, such as organic compounds, that are altered by exposure to light of a particular wavelength or range of wavelengths. Exposure to light makes the photoresist either more or less susceptible to removal by chemical agents. After the layer of photoresist is applied, it is exposed to light, or other electromagnetic radiation, through a mask. Alternatively, the photoresist is patterned under a beam of charged particles, such as electrons. The mask may be a positive or negative mask depending on the nature of the photoresist. The mask includes the desired pattern of working electrodes, which are the electrodes on which the electrocatalytic reactions take place when the detection marker and the redox label are both present and immobilized on the electrode. Once exposed, the portions of the photoresist and the thin film between the working electrode 42 is selectively removed using, for example, standard etching techniques (dry or wet), to leave the isolated working electrode of the array.

The detection working electrode 42 may have a variety of shapes, including, for example, square, rectangular, circular, ovoid, and so forth. For instance, the width (e.g., dimension that is substantially perpendicular to the flow of the test sample) of the electrode 42 may be from about 0.1 to about 10 millimeters, in some embodiments from about 0.5 to about 5 millimeters, and in some embodiments, from about 1 to about 3 millimeters. The surface smoothness and layer thickness of the electrode 42 may also be controlled through a combination of a variety of parameters, such as mesh size, mesh angle, and emulsion thickness when using a printing screen. Emulsion thickness may be varied to adjust wet print thickness. The dried thickness may be slightly less than the wet thickness because of the vaporization of solvents. In some embodiments, for instance, the dried thickness of the printed electrode 42 is less than about 100 microns, in some embodiments less than about 50 microns, in some embodiments less than about 20 microns, in some embodiments less than about 10 microns, and in some embodiments, less than about 5 microns.

In addition, one or more surfaces of the detection working electrode 42 are generally treated with various affinity reagents. Because counter/reference electrode(s) are not disposed on the substrate 80, the detection working electrode 42 may be advantageously treated with such affinity reagents without fear of contaminating the counter/reference electrode (s). This provides greater freedom in the techniques used to apply the affinity reagents. The affinity reagents may be applied to the surface of the detection working electrode 42 using a variety of well-known techniques. For example, the reagents may be directly immobilized on the surface of the electrode 42, may be contained within a substrate that is disposed on the surface of the electrode 42, may be mixed into the materials used to form the electrode 42, and so forth. In one embodiment, the affinity reagents are formulated into a solution and screen-printed, ink-jet printed, drop coated, or sprayed onto the working electrode surface. Screen printing inks, for instance, are typically formulated in a buffer solution (e.g., phosphate buffer) containing the specific or non-specific binding members. Although not required, an organic immobilizing solvent may be added to the aqueous buffer solution to help wet the hydrophobic or non-hydrophilic surfaces. In some embodiments, for example, the solvent may be an alcohol, ether, ester, ketone, or combinations thereof. When coated, the electrode 42 is desirably applied with a uniform coating across its entire surface. The coating is typically a single layer, but multiple layers are also contemplated by the present invention. The coating, regardless of monolayer or multiple layers, is typically optimized to give the largest current and signal/noise ratio.

Upon application to the electrode surface, the reagents may optionally be stabilized. Stabilization facilitates long-term stability, particularly for ensuring required shelf-life incurred during shipping and commercial selling. For instance, in one embodiment, stabilization may be accomplished by coating a layer, such as a polymer, gel, carbohydrate, protein, etc., onto the electrode surface before and/or after application of the affinity reagent(s). Some commercially available examples of such a stabilization coating are Stabilcoat®, Stabilguard®, and Stabilzyme® from Surmodics, Inc. of Eden Prairie, Minn.

One example of an affinity reagent that may be applied to the surface of the detection working electrode 42 is a specific binding capture ligand. The specific binding capture ligand is capable of directly or indirectly binding to the analyte of interest. The specific binding capture ligand typically has a specificity for the analyte of interest at concentrations as low as about $10^{-7}$ moles of the analyte per liter of test sample (moles/liter), in some embodiments as low as about $10^{-8}$ moles/liter, and in some embodiments, as low as about $10^{-9}$ moles/liter. For instance, some suitable immunoreactive specific binding capture ligands may include antigens, haptens, aptamers, antibodies, and complexes thereof, including those formed by recombinant DNA methods or peptide synthesis. Generally speaking, electrochemical stability is desired for accurate analyte detection because any redox response from the specific binding capture ligand may complicate the true current responses from the analyte. Thus, in most embodiments, the specific binding capture ligand is stable at the potential range of from −0.75 to +0.75 Volts, in some embodiments from −0.50 to +0.50 Volts, and in some embodiments, from −0.35 to +0.35 Volts, in comparison with the reference electrode.

Besides specific binding capture ligands, redox mediators may also be applied to the surface of the detection working electrode 42. The redox mediators may be applied to the working electrode 42 at any time, such as during formation of the assay device or during testing. In one embodiment, for instance, the redox mediator is immobilized on the surface of the electrode 42. Alternatively, the redox mediator is applied to the surface only after the test sample reaches the detection zone 31. Some examples of suitable redox mediators that may be used in the present invention include, but are not limited to, oxygen, ferrocene derivatives, quinones, ascorbic acids, redox polymers with metal complexes, glucose, redox hydrogel polymers, organometallic complexes based upon osmium, ruthenium, iron, etc., and so forth. Particular examples of suitable redox mediators include ferricyanide, 2,5-dichloro-1,4-benzoquinone, 2,6-dichloro-1,4-benzoquinone, 2,6-dimethyl-1,4-benzoquinone, phenazine ethosulfate, phenazine methosulfate, phenylenediamine, 1-methoxy-phenazine methosulfate, and 3,3'5,5' tetramethyl benzidine (TMB). Substrates may also be used in conjunction with a soluble redox mediator present in solution. In such instances, the solution-based substrate may be simply placed on the surface of the applicable electrode. Some commercially available examples of such solution-based substrates include 1-Step turbo TMB (Pierce Chemical Co., Rockford, Ill.) and K-Blue Substrate Ready-to-Use (Neogen Corp., Lexington, K.Y.). For instance, "K-Blue Substrate" is a chromogenic substrate for horseradish peroxidase that contains 3,3',5,5' tetramethylbenzidine (TMB) and hydrogen peroxide ($H_2O_2$). Other suitable redox mediators are described in U.S. Pat. Nos. 6,281,006 to Heller, et al.; 5,508,171 to Walling, et al.; 6,080,391 to Tsuchiya, et al.; and 6,461,496 to Feldman, et al., which are incorporated herein in their entirety by reference thereto for all purposes. As will be readily recognized by those skilled in the art, many other different reaction mechanisms may be used in the present invention to achieve the electrolysis of an analyte through a reaction pathway incorporating a redox mediator.

As indicated above, the substrate 80 may optionally include a calibration working electrode 44. When utilized, the calibration working electrode 44 may enhance the accuracy of the analyte concentration determination. For instance, a current will generally be generated at the calibration working electrode 44 that corresponds to intrinsic background interference stemming from the counter and reference electrodes, as well as the working electrodes themselves. Once determined, the value of this intrinsic background current may be used to calibrate the measured current value at the detection working electrode 42 to obtain a more accurate reading. The calibration working electrode 44 may generally be formed as described above with respect to the detection working electrode 42. In fact, because the calibration working electrode 44 is configured to calibrate the detection working electrode 42, it is generally desired that such electrodes are formed in approximately the same manner, from the same materials, and to have the same shape and/or size.

The detection and calibration working electrodes 42 and 44 are also generally applied with the same surface treatments to improve the calibration accuracy. However, one primary difference between the detection working electrode 42 and the calibration working electrode 44 is that the electrode 44 does not typically contain a specific binding capture ligand for the analyte of interest. This allows most, if not all, of the analyte to bind to the electrode 42, thereby enabling the electrode 42 to be used primarily for detection and the electrode 44 to be used primarily for calibration.

For example, the use of this calibration electrode 44 would help determine if non-specific binding was occurring on the electrode surfaces. In some instances, non-specific binding of the redox label or other current-generating compounds to the capture ligand present on the detection working electrode 42 may create inaccuracies in the measured current. Contrary to the specific binding ligands, the non-specific binding ligands do not have a high specificity for the analyte of interest. In fact, the non-specific binding capture ligand typically has no specificity for the analyte of interest at concentrations as high as about $10^{-2}$ moles of the analyte per liter of test sample (moles/liter), and in some embodiments, as high as about $10^{-3}$ moles/liter. The non-specific binding ligands may form bonds with various immunoreactive compounds. These immunoreactive compounds may have a redox center or may have inadvertently been provided with a redox center through attachment of a redox compound (e.g., enzyme). Without the calibration working electrode 44, these immunoreactive compounds would thus generate a low level of current detected from the detection working electrode 42, which causes error in the resulting analyte concentration calculated from the generated current. This error may be substantial, particularly when the test sample contains a low analyte concentration.

To minimize any undesired binding (including non-specific binding as described above) on the surfaces of the working electrodes 42 and 44, a blocking agent may be applied thereto. The term "blocking agent" means a reagent that adheres to the electrode surface so that it "blocks" or prevents certain materials from binding to the surface. Blocking agents may include, but are not limited to, β-casein, Hammerstern-grade casein, albumins such as bovine serum albumin, gelatin, pluronic or other surfactants, polyethylene glycol, polyvinyl pyrrolidone or sulfur derivatives of the above compounds, a surfactant such as Tween 20, 30, 40 or Triton X-100, a polymer such as polyvinyl alcohol, and any other blocking material known to those of ordinary skill in the art. This includes commercial blends, such as SuperBlock® or SEA BLOCK (Pierce Chemical Co., Rockford, Ill.) or Heterophilic Blocking Reagent (Scantibodies, Santee, Calif.). Depending on the conductive materials used for preparing the working electrodes, the blocking agents may be formulated to adapt to the electrode surface properties. In some embodiments, a cocktail containing multiple blocking agents may be applied onto an electrode and incubated for 5 to 30 minutes, and any excess solution may be removed and the resulting electrode thoroughly dried.

Figure 2:
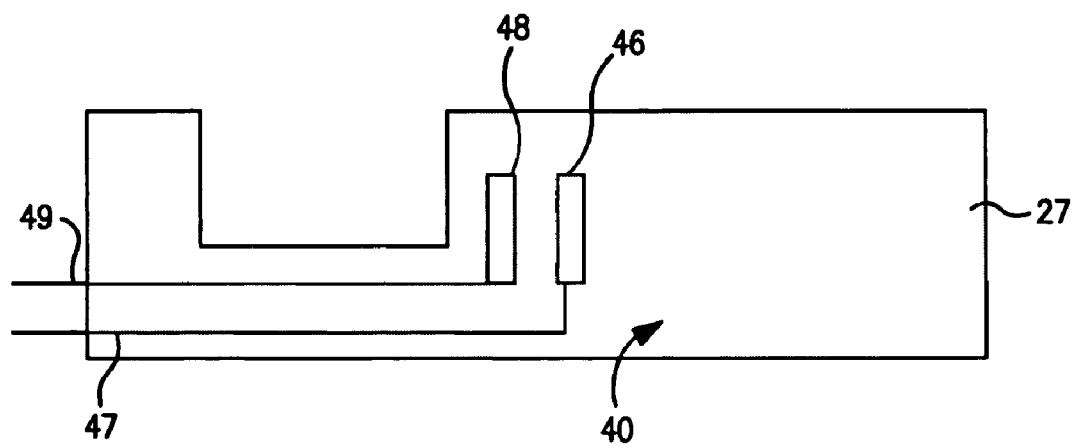
FIG. 2 is a schematic illustration of a substrate containing auxiliary electrodes for use in one embodiment of an assay device of the present invention.

Referring to FIG. 2, one embodiment of a second substrate 40 is illustrated that may be used in the assay device of the present invention. The second substrate 40 may be formed from the same type of materials as the first substrate 80, or from different materials. The substrate 40 has a surface 27 on which is disposed one or more auxiliary electrodes, such as a reference electrode 46 and a counter electrode 48. If desired, the reference and counter electrodes 46 and 48 may be combined into a single "pseudo" electrode. This may be particularly beneficial when the solution resistance is negligible or the generated current is relatively small. Moreover, it should be understood that separate counter and working electrodes may be provided for each working electrode 42 and 44. The reference and counter electrodes 46 and 48 may be formed in a manner such as described above, or using any other method known to those skilled in the art. To minimize any undesired binding on the surfaces of the electrodes 46 and 48, a blocking agent may also be applied such as described above.

Figure 5:
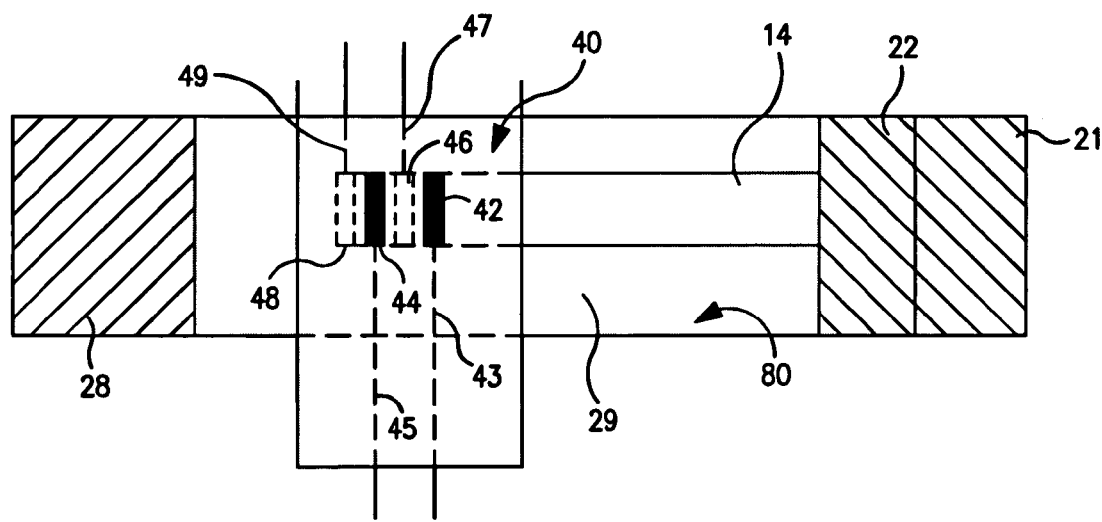
FIG. 5 is a schematic illustration of another embodiment of an assay device formed according to the present invention.

The leads for the electrodes may generally be positioned in any desired manner as is readily appreciated by those skilled in the art. Referring to FIGS. 1-2, for instance, the leads 43 and 45 for the electrodes 42 and 44, respectively, are positioned on the first substrate 80, while the leads 47 and 49 for the electrodes 46 and 48, respectively, are positioned on the second substrate 40. In the illustrated embodiment, the leads 43, 45, 47, and 49 are positioned parallel to the flow of the test sample. Alternatively, the leads 43, 45, 47, and/or 49 may be positioned perpendicular to the flow of the test sample. For example, FIG. 5 illustrates an embodiment in which the leads 43, 45, 47 and 49 are positioned perpendicular to the flow of the test sample.

A variety of other components may also be employed on the first and/or second substrates 40 and 80. For example, in one embodiment, several flow-control mechanisms are used in conjunction with the first substrate 80, although it should be understood that such mechanisms may also be used in conjunction with the first substrate 40. For example, an absorbent wicking pad 28 is disposed at one end of the substrate 80 to promote capillary action and fluid flow of the sample. To ensure that the absorbent wicking pad 28 does not inhibit the ability of the electrodes from being placed sufficiently close to each other upon formation of the assay device, the first substrate 40 may define a cut-out region that corresponds to the size and shape of the absorbent wicking pad 28. Thus, when the substrates 40 and 80 are placed in a face-to-face relationship, the absorbent wicking pad 28 fits into the cut-out region.

In addition, a sample channel 14 is also formed on the substrate 80. Multiple sample channels 14 may be utilized for multiple test samples. The sample channel 14 may be formed from any of a variety of materials through which the test sample is capable of flowing. In most embodiments, it is desired that a dielectric material be used to form the sample channel 14 to reduce unwanted interference with the electrochemical detection of the analyte. The term "dielectric" material generally refers to a material having a dielectric constant "k" of less than about 5 at 1 kHz (defined by ASTM D150-98 Standard Test Methods for AC Loss Characteristics and Permittivity (Dielectric Constant) of Solid Electrical Insulation, an insulation resistance of greater than 10 GΩ/mil, and/or a breakdown voltage of greater than 1000 V/mil DC (also defined by ASTM D150-98 Standard Test Methods for AC Loss Characteristics and Permittivity (Dielectric Constant) of Solid Electrical Insulation. For example, a wide variety of organic and inorganic polymers, both natural and synthetic may be employed as a dielectric material for the sample channel 14. Examples of such polymers include, but are not limited to, polyesters, polyimides, polyamides, polycarbonates, polyolefins (e.g., polyethylene, polypropylene, etc.), polysiloxanes, polyurethanes, polyvinylchlorides, polystyrenes, and so forth. Commercial dielectric materials, such as 5036 Heat Seal/Encapsulant, 5018 UV curable dielectric, 5018G UV curable dielectric and 5018A UV curable dielectric are available from DuPont Biosensor Group of Research Triangle Park, N.C.

If desired, such a polymeric channel may be formed by first applying monomer(s) or pre-polymer(s) for the polymer, and then polymerizing the monomer(s) or pre-polymer(s) using well-known techniques, such as heating, irradiating, etc. For example, polymerization may be induced with ionizing radiation, which is radiation having an energy sufficient to either directly or indirectly produce ions in a medium. Some suitable examples of ionizing radiation that may be used in the present invention include, but are not limited to, ultraviolet radiation, electron beam radiation, natural and artificial radio isotopes (e.g., $\alpha$, $\beta$, and $\gamma$ rays), x-rays, neutron beams, positively charged beams, laser beams, and so forth. Electron beam radiation, for instance, involves the production of accelerated electrons by an electron beam device. Electron beam devices are generally well known in the art. For instance, examples of suitable electron beam devices are described in U.S. Pat. Nos. 5,003,178 to Livesay; 5,962,995 to Avnery; 6,407,492 to Avnery, et al., which are incorporated herein in their entirety by reference thereto for all purposes.

The geometry of the sample channel 14 may be selected so that capillary forces assist the flow of the test sample through the sample channel 14. For example, the sample channel 14 may have a cross-sectional shape that is circular, square, rectangular, triangular, v-shaped, u-shaped, hexagonal, octagonal, irregular, and so forth. The sample channel 14 may also be continuous or discontinuous, and may also contain continuous or discontinuous sample mixing islands to promote sample mixing. Further, in some embodiments, the sample channel 14 may be a "microchannel", which is a channel that allows for fluid flow in the low Reynolds number region where fluid dynamics are dominated by viscous forces rather than inertial forces. The formula for Reynolds number is as follows:

$$Re = \rho \delta^2 / \eta \tau + \rho \mu \delta / \eta$$

wherein, $\mu$ is the velocity vector, $\rho$ is the fluid density, $\eta$ is the viscosity of the fluid, $\delta$ is the characteristic dimension of the channel (e.g., diameter, width, etc.), and $\tau$ is the time scale over which the velocity changes (where $\mu/\tau = \delta\mu/dt$). Fluid flow behavior at steady state ($\tau \to \infty$) is characterized by the Reynolds number, $Re = \rho\mu\delta/\eta$. Due to their small size and slow velocity, microchannels often allow fluids to flow in the low Reynolds number regime (Re less than about 1). In this regime, inertial effects, which cause turbulence and secondary flows, are negligible, and viscous effects dominate the dynamics so that flow is generally laminar. Thus, to maintain laminar flow, it is sometimes desired that the characteristic dimension of the channel range from about 0.5 micrometers and about 500 micrometers, in some embodiments from about 1 micrometer to about 200 micrometers, and in some embodiments, from about 5 micrometers to about 10 micrometers.

The height or depth of the sample channel 14 may also vary to accommodate different volumes of the test sample. The sample channel 14 may contain opposing walls that are raised a certain height above the surface 29 of the substrate 80. For example, the walls may have a height of from about 0.1 to about 500 micrometers, in some embodiments from about 0.5 to about 250 micrometers, and in some embodiments, from about 1 to about 100 micrometers. In some embodiments, the height of the sample channel 14 is the combination of the printed channel and an adhesive layer (e.g., glue, double-sided tape, etc.) used, for instance, to laminate a porous membrane over the printed channel. The thickness of the adhesive layer may vary, for instance, from about 10 to about 100 microns. Likewise, the length of the sample channel 14 may also vary. For example, the sample channel 14 may have a length that is from about 1 millimeter to about 50 centimeters, and in some embodiments, from about 5 millimeters to about 50 millimeters.

Printing techniques are generally utilized in the present invention to apply the sample channel 14 due to their practical and cost-saving benefits. For instance, several suitable printing techniques are described in U.S. Pat. Nos. 5,512,131 to Kumar, et al.; 5,922,550 to Everhart, et al.; 6,294,392 to Kuhr, et al.; 6,509,085 to Kennedy; and 6,573,040 to Everhart, et al., which are incorporated herein in their entirety by reference thereto for all purposes. For example, in one embodiment, "stamp printing" is utilized to apply the sample channel 14. Some suitable stamp printing techniques are described in U.S. Pat. Nos. 5,512,131 to Kumar, et al. and 5,922,550 to Everhart, et al. For example, an elastomeric stamp may be used to transfer the ink to the substrate surface through contact. The stamp is fabricated by casting polydimethylsiloxane (PDMS) on a master having the inverse of the desired print pattern, which will thereby result in the desired channel pattern. Masters are prepared using standard photolithographic techniques, or constructed from existing materials having microscale surface features. In one embodiment, a photolithographically-produced master is placed in a glass or plastic Petri dish, and a mixture of SYLGARD® silicone elastomer 184 and SYLGARD® silicone elastomer 184 curing agent (Dow Corning Corporation) is poured over it. The polydimethylsiloxane (PDMS) elastomer is allowed to sit at room temperature and is then cured; alternately, for faster curing, the elastomer may be cured at a temperature of from about 60 to about 65° C. When cured, PDMS is sufficiently elastomeric to allow good conformal contact of the stamp and the surface of the substrate 40.

The resulting elastomeric stamp is "inked" by exposing the stamp to a solution of the desired material used to help form the fluidic channel. This is typically done by placing the stamp face down in the solution for about 10 seconds to about 10 minutes. The stamp is allowed to dry, either under ambient conditions or by exposure to a stream of air or nitrogen gas. Following inking, the stamp is applied to the surface of the substrate 40. Light pressure is used to ensure complete contact between the stamp and the substrate 40. After about 1 second to about 5 minutes, the stamp is then gently peeled from the substrate 40. Following removal of the stamp, the substrate 40 may be rinsed and dried.

Stamp printing, such as described above, may be used to prepare channels in various ways. In one embodiment, for example, the elastomeric stamp is inked with a material that significantly alters the surface energy of the substrate so that it may be selectively "wettable" to the monomer or pre-polymer (if post-cured), or polymer used to make the channel. The stamp could have raised features to print the desired channel pattern. An exemplary stamp printing method may involve inking the stamp with a wetting agent, such as hydrophilic self-assembling monolayers (SAMs), including those that are carboxy-terminated. Various examples of such self-assembling monolayers are described in U.S. Pat. No. 5,922,550 to Everhart, et al. In another embodiment, hydrophobic wetting agents may be utilized. Specifically, the inverse of the desired pattern is stamp printed onto a hydrophilic substrate. Upon exposure of the monomer or pre-polymer (if post-cured), or polymer, the inks would selectively wet only on the substrate 40, thereby resulting in the desired channel pattern. Another stamp printing technique might simply involve inking an elastomeric stamp with a solution of the monomer or pre-polymer (if post-cured), or polymer. The stamp may have raised features to match the desired channel pattern so that a direct transfer of the channel-forming material would occur on the substrate 40.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the fluidic channels are to be printed. The print material is painted onto the screen, and transferred by rubbing the screen (which is in contact with the substrate) with a squeegee.

In addition to contact printing, any of a variety of well-known non-contact printing techniques may also be employed in the present invention. In one embodiment, for example, ink-jet printing may be employed. Ink-jet printing is a non-contact printing technique that involves forcing ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

In addition to the printing techniques mentioned above, any other suitable printing technique may be used in the present invention. For example, other suitable printing techniques may include, but not limited to, such as laser printing, thermal ribbon printing, piston printing, spray printing, flexographic printing, gravure printing, etc. Such techniques are well known to those skilled in the art.

Besides the sample channel 14, the substrate 80 may also include other channels that serve a variety of purposes. For example, the substrate 80 may include a washing channel (not shown) that provides for the flow of a washing reagent to the detection working electrode 42 to remove any redox labels (described below) that remain unbound. Examples of washing agents may include, for instance, water, a buffer solution, such as PBS buffer, HEPES buffer, etc., and so forth. In addition, a reagent channel (not shown) may also be provided through which affinity reagents (e.g., capture ligands, redox mediators, particles, labels, etc.) may flow to initiate a desired electrochemical reaction. If desired, the additional washing channel and reagent channel may be printed in the manner described above. By using separate and distinct sample addition, washing, and reagent channels, the controlled and sequential delivery of different solutions may be provided.

Other techniques may also be employed in conjunction with, or in lieu of, the sample channel 14. In one embodiment, for example, a porous membrane or mesh (not shown) may be disposed on the substrate 40 and/or 80 that acts as a fluidic medium to transport the test sample to the detection working electrode 42. The pores of the membrane help guide the test sample to the detection working electrode 42 and may also help facilitate uniform mixing. In some cases, it may be desired that the "flow time" of the test sample through the membrane be long enough to promote uniform mixing and ensure that the analyte within the test sample has sufficient time to react with the desired reagents. For example, the time for the test sample to contact the detection working electrode 42 upon application may be at least about 1 minute, in some embodiments at least about 2 minutes, in some embodiments from about 3 to about 10 minutes, and in some embodiments, from about 4 to about 8 minutes. Such enhanced flow times are not only possible for test samples with high volumes, but also for test samples with low volumes. For example, test samples having a volume of less than about 100 microliters, in some embodiments from about 0.55 to about 50 microliters, and in some embodiments, from about 5 to about 35 microliters, may have an enhanced flow time. The ability to use such small test sample volumes is beneficial in that larger test volumes often increase background interference.

Without intending to be limited by theory, it is believed that the ability to achieve a long flow time for test samples with low volumes is a consequence of selectively controlling certain properties of the membrane, such as the shape or size of the membrane, the size of the pores, the material from which the membrane is formed (including its surface energy), etc. For example, the membrane may be selected to have any desired shape, such as a generally rectangular, square, circular, or any other regular or irregular shape. In some cases, one shape, such as a rectangular shape, may provide a longer flow time than another shape, such as a circular shape. Specifically, a generally rectangular membrane may have a long length (e.g., dimension that is substantially parallel to the flow of the test sample) and a small width (e.g., dimension that is substantially perpendicular to the flow of the test sample) to impart a slower flow rate. In some embodiments, for example, the width of a generally rectangular membrane may be from about 0.5 to about 10 millimeters, in some embodiments from about 1 to about 5 millimeters, and in some embodiments, from about 1 to about 3 millimeters. The length of such a membrane may be from about 1 to about 40 millimeters, in some embodiments from about 1 to about 20 millimeters, and in some embodiments, from about 1 to about 5 millimeters. The size of the pores may also affect the flow time of a test sample through the membrane. Specifically, smaller pore sizes often result in slower flow rates. In most embodiments, the pores of the membrane have an average size of from about 1 micron to about 50 microns, in some embodiments from about 5 microns to about 30 microns, and in some embodiments from about 5 microns to about 15 microns. If desired, one or more dimensions of the membrane may be selected to correspond to a dimension of the detection working electrode 42. In this manner, most if not all of the test sample flowing through the membrane will contact a surface of the electrode 42, which alleviates possible background interference that might otherwise result due to the test sample flowing around the edges of the electrode 42. Alternatively, the electrode 42 and membrane may have different "actual" widths, but have substantially the same "effective" widths in that the portion of their widths exposed to the flow of the test sample is substantially the same. For instance, the width of the membrane may actually be larger than the width of the electrode 42. Nevertheless, the portion of the membrane's width that is larger than that of the electrode 42 may be blocked to the flow of the test sample using, for instance, tape.

The materials used to form the membrane may also affect the flow time of the test sample. Some examples of suitable materials used to form the porous membrane may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. Without intending to be limited by theory, it is believed that the rate at which the test sample flows through the membrane may be greater for materials that are more hydrophilic in nature. Thus, for membranes of approximately the same pore size, shape, and dimensions, those made of nitrocellulose may result in a faster flow time than those made of polyvinylidene fluoride, which is somewhat less hydrophilic than nitrocellulose.

Referring again to FIG. 1, the substrate 80 also contains a sample pad 21 to which a test sample may be applied. Some suitable materials that may be used to form the sample pad 21 include, but are not limited to, nitrocellulose, cellulose, porous polyethylene pads, and glass fiber filter paper. If desired, the sample pad 21 may also contain one or more assay pretreatment reagents, either covalently or non-covalently attached thereto. In the illustrated embodiment, the test sample travels from the sample pad 21 to an optional conjugate pad 22 that is placed in communication with one end of the sample pad 21. The conjugate pad 22 is formed from a material through which the test sample is capable of passing. For example, in one embodiment, the conjugate pad 22 is formed from glass fibers. Although the analyte of interest may be inherently capable of undergoing the desired oxidation/reduction reactions because it contains a redox center, it may be desired, in other embodiments, to attach a redox label to the analyte. The redox label may be applied at various locations of the device 20, such as to the conjugate pad 22, where it may bind to the analyte of interest before reaching the sample channel 14. Although only one conjugate pad 22 is shown, it should be understood that additional conjugate pads may also be used in the present invention. Besides the conjugate pad 22, the analyte may be bound to a redox label within the sample channel 14 or any other location of the assay device 20, or even prior to being applied to the device 20.

Figure 6:
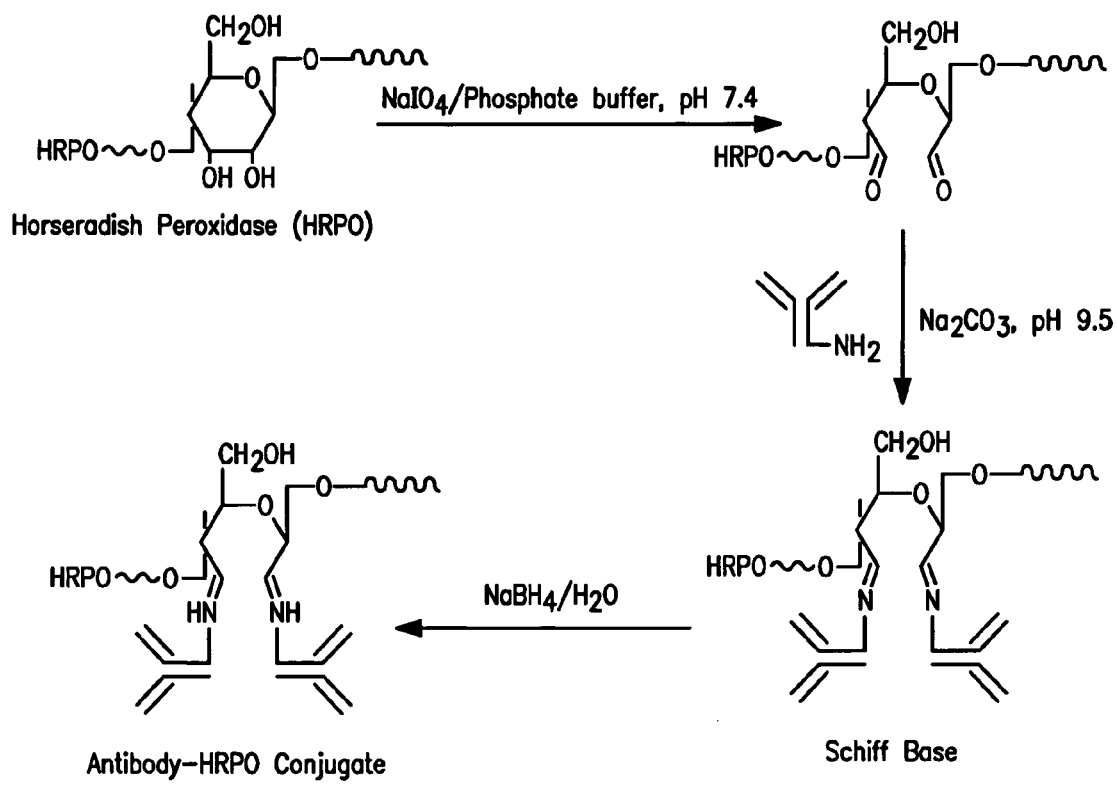
FIG. 6 illustrates the "periodate" method of forming a horseradish peroxidase (HRP) conjugate for use in one embodiment of the present invention.

The term "redox label" refers to a compound that has one or more chemical functionalities (i.e., redox centers) that may be oxidized and reduced. Such redox labels are well known in the art and may include, for instance, an enzyme such as alkaline phosphatase (AP), horseradish peroxidase (HRP), glucose oxidase, beta-galactosidase, urease, and so forth. Other organic and inorganic redox compounds are described in U.S. Pat. Nos. 5,508,171 to Walling, et al.; 5,534,132 to Vreeke, et al.; 6,241,863 to Monboucuette; and 6,281,006 to Heller, et al., which are incorporated herein in their entirety by reference thereto for all purposes. Horseradish peroxidase (HRP), for instance, is an enzyme that is commonly employed in electrochemical affinity assay devices. Two methods are commonly used for the preparation of antibody-coupled horseradish peroxidase (HRP) conjugates, i.e., "glutaraldehyde" and "periodate" oxidation. As is known in the art, the "glutaraladehyde" method involves two steps and results in high molecular weight aggregates. Further, the "periodate" method involves three steps. For instance, as shown in FIG. 6, the "periodate" method may reduce interference of HRP active-site amino groups because it is only conjugated through carbohydrate moieties. Specifically, the "periodate" method opens up the carbohydrate moiety of the HRP glycoprotein molecule to form aldehyde groups that will form Schiff bases with antibody amino groups. Thus, although not required, it may be desired to use HRP formed by the "periodate" method to minimize background current.

Besides being directly attached to the analyte, the redox label may also be indirectly attached to the analyte through a specific binding member for the analyte. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies, and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The redox labels may be used in a variety of ways to form a probe. For example, the redox labels may be used alone to form probes. Alternatively, the redox labels may be used in conjunction with polymers, liposomes, dendrimers, and other micro- or nano-scale structures to form probes. For example, the redox labels may be used in conjunction with particles (sometimes referred to as "beads") to form the probes. Naturally occurring particles, such as nuclei, mycoplasma, plasmids, plastids, mammalian cells (e.g., erythrocyte ghosts), unicellular microorganisms (e.g., bacteria), polysaccharides (e.g., agarose), and so forth, may be used. Further, synthetic particles may also be utilized. For example, in one embodiment, latex particles are utilized. Although any latex particle may be used in the present invention, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. Nos. 5,670,381 to Jou, et al. and 5,252,459 to Tarcha, et al., which are incorporated herein in their entirety by reference thereto for all purposes. In addition, inorganic particles, such as colloidal metallic particles (e.g., gold) and non-metallic particles, carbon particles, and so forth, may also be utilized. The mean diameter of the particles may generally vary as desired. For example, in some embodiments, the mean diameter of the particles may range from about 0.01 microns to about 1,000 microns, in some embodiments from about 0.01 microns to about 100 microns, and in some embodiments, from about 0.01 microns to about 10 microns. In one particular embodiment, the particles have a mean diameter of from about 0.01 to about 2 microns. Generally, the particles are substantially spherical in shape, although other shapes including, but not limited to, plates, rods, bars, irregular shapes, etc., are suitable for use in the present invention. As will be appreciated by those skilled in the art, the composition, shape, size, and/or density of the particles may widely vary.

Figure 3:
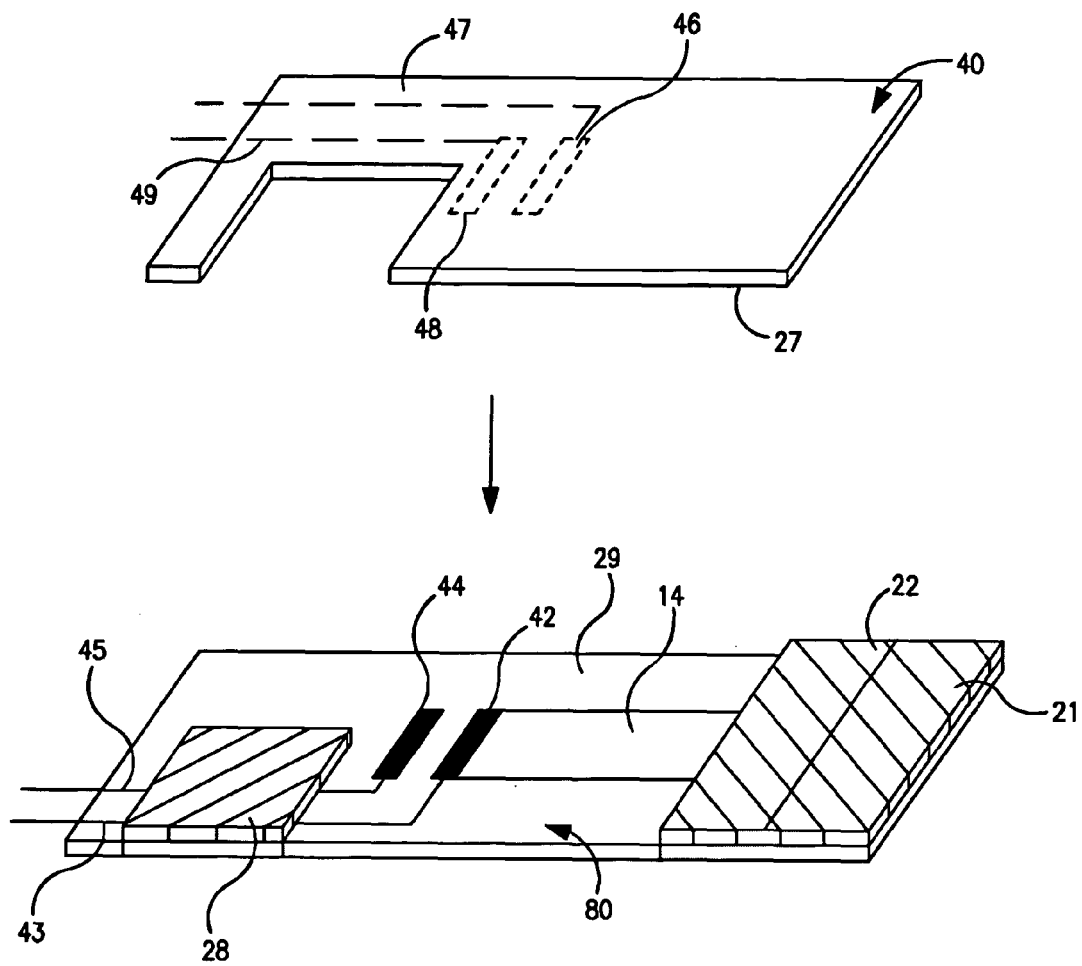
FIG. 3 is a schematic illustration of one embodiment for forming an assay device from the substrates of FIGS. 1 and 2.
Figure 4:
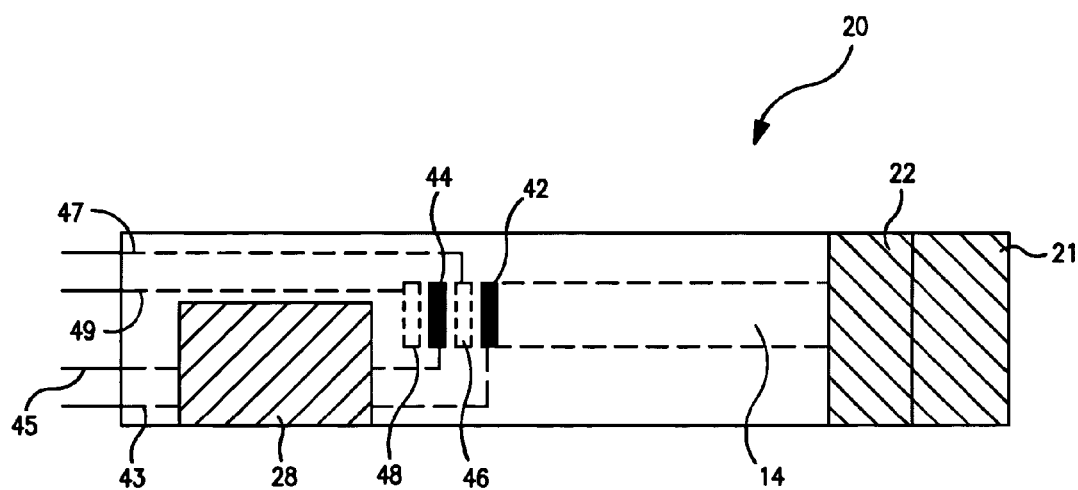
FIG. 4 is a schematic illustration of the assay device formed according to FIG. 3.

Referring to FIGS. 3-5, various embodiments for forming an assay device 20 from the substrates 40 and 80 will now be described in more detail. Although not required, it is generally desired that the substrates 40 and 80 be laminated in such a manner that the detection working electrode 42 is adjacent to and in electrical communication with, but does not contact, the reference and counter electrodes 46 and 48. Thus, as shown in FIG. 3, the surface 27 of the substrate 40 is placed over the surface 29 of the substrate 80 to form the laminate assay device 20. In the embodiment shown in FIGS. 3-4, the substrates 40 and 80 are aligned substantially parallel to each other. In the embodiment shown in FIG. 5, the substrates 40 and 80 are aligned substantially perpendicular to each other. It should be understood, however, that the present invention is not limited to any particular alignment or configuration of the laminated substrates.

The geometric relationship between the electrodes may also vary. For example, the electrodes may be aligned in any order capable of generating the desired detection current. Likewise, each electrode may be positioned at any desired angle to the flow of the test sample. In the embodiments shown in FIGS. 3-5, the substrates 40 and 80 are laminated such that the working electrode 42 is positioned adjacent to the reference electrode 46, the reference electrode 46 is positioned adjacent to the calibration working electrode 44, and the calibration working electrode 44 is positioned adjacent to the counter electrode 48. Moreover, each electrode is also positioned perpendicular to the flow of the test sample. Of course, various other electrode configuration and/or geometric relationships may be utilized in the present invention.

Regardless of the particular configuration of the electrodes, the present inventors have discovered that the use of separate substrates 40 and 80 may substantially reduce background interference. Specifically, the use of separate substrates allows the working electrodes 42 and 44 to be treated with affinity reagents without regard to potential contamination of the reference and counter electrodes 46 and 48 that would otherwise cause background interference. Once the treatment process is complete, the reference and counter electrodes 46 and 48 may then be placed in the desired location. Although not required, the laminated substrates 40 and 80 may be laminated in the desired position using any well-sealing sealing technique, such as by adhesively attaching the substrates 40 and 80 with glue, double-sided tape, and so forth. The extent that the substrates 40 and 80 are laminated together may vary as desired. For example, in some embodiments, the entire periphery of the substrates 40 and 80 are adhesively attached.

Various embodiments of detection the presence of an analyte within a test sample using the assay device 20 of FIG. 4 or 5 will now be described in more detail. It should be understood, however, that the embodiments discussed below are only exemplary, and that other detection techniques and assay device configurations are also contemplated by the present invention. To initiate the detection of an analyte within a test sample, a user may simply apply the test sample to the sample pad 21 through which it may then travel. From the sample pad 21, the test sample then travels to the conjugate pad 22 where any analyte within the test sample mixes with and attaches to a redox label. In one embodiment, for instance, the label is horseradish peroxidase (HRP) and the analyte of interest is glucose. Because the conjugate pad 22 is in fluid communication with the sample channel 14, the labeled analyte may migrate from the conjugate pad 22 to the channel 14 through which it travels for the desired amount of time until it reaches the detection working electrode 42, where the labeled analyte binds to the specific binding capture ligand and reacts with a redox mediator. In one embodiment, for example, the analyte is reacted as follows:

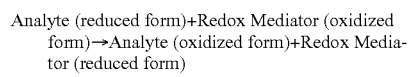
Analyte (reduced form)+Redox Mediator (oxidized form)→Analyte (oxidized form)+Redox Mediator (reduced form)

In addition, non-specific binding may be monitored and corrected using the optional calibration working electrode 44. It is intended that the amount of non-analyte materials that bind to the calibration working electrode 44 will be similar to the amount of non-analyte material that non-specifically binds to the detection working electrode 42. Thus, in this manner, the background signal due to non-specific binding may be compensated. In one embodiment, for example, the non-analyte biological materials (abbreviated "NAB") are reacted as follows:

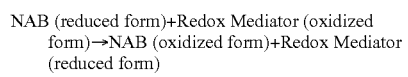
NAB (reduced form)+Redox Mediator (oxidized form)→NAB (oxidized form)+Redox Mediator (reduced form)

Detection techniques, such as amperometric, couloumetric, voltammetric, etc., may then be used to detect the analyte. A further description of such electrochemical detection techniques is described in *Electrochemical Methods*, A. J. Bard and L. R. Faulner, John Wiley & Sons (1980). In one embodiment, for example, a potentiostat or reader may apply a potential difference between the detection working electrode 42 and counter electrode 46. When the potential difference is applied, the amount of the oxidized form of the redox mediator at the counter electrode 46 and the potential difference is sufficient to cause diffusion limited electro-oxidation of the reduced form of the redox mediator at the surface of the detection working electrode 42. The magnitude of the required potential is thus dependent on the redox mediator.

Namely, the potential is typically large enough to drive the electrochemical reaction to or near completion, but not large enough to induce significant electrochemical reaction of interferents, such as urate, ascorbate, and acetaminophen, that may affect the current measurements. Similarly, the potential difference may also be supplied between the optional calibration working electrode 44 and counter electrode 46. When the potential difference is applied, diffusion limited electro-oxidation of the reduced form of the redox mediator occurs at the surface of the calibration working electrode 44.

Generally, the detection and calibration working electrodes 42 and 44 simultaneously generate a respective signal from a single measurement of a sample. The simultaneously generated signals are averaged by a processing circuit, such as a multi-channel potentiostat. Multi-channel potentiostats are well known in the art, and are described, for instance, in U.S. Pat. No. 5,672,256 to Yee, which is incorporated herein in its entirety by reference thereto for all purposes. Each channel of a multi-channel potentiostat may function as a potentiostat, and thus may be associated with its own reference and/or counter electrode, or may share reference and/or counter electrodes. One suitable example of a multi-channel potentiostat that may be used in the present invention is commercially available under the name "MSTAT" from Arbin Instruments, Inc. of College Station, Tex. Once detected, the current measured at the detection working electrode 42 is calibrated by the current measured at the calibration working electrode 44 to obtain a calibrated current reading that may be correlated to the concentration of analyte in the sample. The correlation may result from predetermined empirical data or an algorithm, as is well known in the art. If desired, the generated current and analyte concentration may be plotted as a curve to aid in the correlation therebetween. As a result, calibration and sample testing may be conducted under approximately the same conditions at the same time, thus providing reliable quantitative or semi-quantitative results, with increased sensitivity. In the case of a sandwich assay format, the signal provided by the detection working electrode 42 is directly proportional to the analyte concentration in the test sample. In the case of a competitive assay format, which may, for instance, be constructed by applying a labeled analyte on the surface of the detection working electrode 42, the signal provided by the detection working electrode 42 is inversely proportional to the analyte concentration in the test sample. It should be understood that the potential may be applied either before or after the sample has been placed in the detection area (e.g. electrodes). The potential is preferably applied after the sample has reached the detection area to prevent continued electrochemical process during the formation of immunocomplex on the electrode surface. The formation time may be from about 1 second to about 15 minutes, depending on the sample size, channel, size, membrane size, and/or electrode size.

Due to the use of separate substrates, the present invention may also easily accommodate more than one analyte. For example, in one embodiment, the auxiliary electrode on the second substrate 80 may be an additional detection working electrode. The detection working electrodes on the substrates 40 and 80 may be used to detection different analytes, and may consequently be treated with different affinity reagents. The counter/reference electrode(s) for each detection working electrode may be present on the substrates 40 and/or 80, or may remain altogether separate, such as being disposed on an additional substrate.

Various parameters of the detection technique may be utilized to improve the consistency and accuracy of the assay device. For example, variations of fabrication processes, such as electrode coating, flow control, sample size, mediator efficiency, etc, may have an impact on data collection. Thus, in one embodiment, the time at which current readings are measured may be selected to achieve improved results. Specifically, when a potential is applied, the initial reading of the current may be inaccurate or less reliable. Accordingly, the time at which the current reading is first recorded may be after applying the potential. Thus, in some embodiments, the first recording is from about 0.001 seconds to about 10 minutes, in some embodiments from about 0.1 seconds to about 1 minute, in some embodiments from about 0.5 to about 20 seconds, and in some embodiments, from about 1 to about 10 seconds, after applying the potential. In addition, the current readings may also be recorded in flexible time intervals. If desired, for example, the number of readings taken at the beginning of the recordings may be greater than the number taken at the end. This is due primarily to the fact that, at the later stages of the recordings, the decrease in measured current is usually more profound than the magnitude of the potential pulse.

Regardless of the detection environment, the total charge is normally the same for a given analyte concentration because the current measurements are obtained at intervals over the course of the entire assay and integrated over time to obtain the total amount of charge, Q, passed to or from the electrode. Q is then used to calculate the concentration of the analyte. For instance, the total charge, Q, may be directly calculated when the redox label is able to generate a detection signal. The completion of the electrochemical reaction is signaled when the current reaches a steady-state value that indicates all or nearly all of the redox labels on the electrode surface have been electrolyzed. In such cases, at least 90%, in some embodiments at least 95%, and in some embodiments, at least 99% of the complexes are electrolyzed. In other cases, however, the redox label may not be able to generate a measurable detection signal without amplification. For instance, an enzyme label may require a substrate to provide amplification of the detection current. If desired, the substrate may be used in excess to ensure that the detection signal reaches the a measurable level. In some embodiments, for example, the ratio of the substrate to the complexes formed on the electrode surface is at least 10:1, in some embodiments at least 100:1, in some embodiments at least 1,000:1, and in some embodiments, at least 10,000:1.

Although various embodiments of assay formats and devices have been described above, it should be understood, that the present invention may utilize any assay format or device desired, and need not contain all of the components described above. Further, other well-known components of assay formats or devices not specifically referred to herein may also be utilized in the present invention. For example, various assay formats and/or devices are described in U.S. Pat. Nos. 5,508,171 to Walling, et al.; 5,534,132 to Vreeke, et al.; 6,241,863 to Monboucuette; 6,270,637 to Crismore, et al.; 6,281,006 to Heller, et al.; and 6,461,496 to Feldman, et al., which are incorporated herein in their entirety by reference thereto for all purposes.

In addition, it should be understood that both sandwich and competitive assay formats may be formed according to the present invention. Techniques and configurations of sandwich and competitive assay formats are well known to those skilled in the art. For instance, sandwich assay formats typically involve mixing the test sample with labeled antibodies so that complexes of the analyte and the labeled antibody are formed. These labeled complexes contact a detection zone where they bind to another antibody and become immobilized, thereby indicating the presence of the analyte. Some examples of such sandwich-type assays are described by U.S. Pat. Nos. 4,168,146 to Grubb, et al. and 4,366,241 to Tom, et al., which are incorporated herein in their entirety by reference thereto for all purposes. In a competitive assay, a labeled analyte or analyte-analog competes with an unlabeled analyte in the test sample for binding to an antibody immobilized at the detection zone. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liofta, and 5,208,535 to Buechler, et al., which are incorporated herein in their entirety by reference thereto for all purposes.

The present invention provides a low-cost, flow-through assay device that may provide accurate analyte detection. The assay devices of the present invention may be produced as a single test for detecting an analyte or it may be formatted as a multiple test device. The uses for the assay devices of the present invention include, but are not limited to, detection of chemical or biological contamination in garments, such as diapers, the detection of contamination by microorganisms in prepacked foods such as fruit juices or other beverages, and the use of the assay devices of the present invention in health diagnostic applications such as diagnostic kits for the detection of antigens, microorganisms, and blood constituents. It should be appreciated that the present invention is not limited to any particular use or application.

The present invention may be better understood with reference to the following examples.

Example 1

The ability to form laminated assay devices, such as shown in FIGS. 1-4, was demonstrated.

The bottom strips: The bottom strips were formed from a Mylar® plastic substrate available from DuPont. The substrate had a thickness of 0.25 to 0.38 millimeters, a length of 5 centimeters, and a width of 1.3 centimeters. The substrate was initially printed with a silver ink line (5000) obtained from DuPont Biosensor Group of Research Triangle Park, N.C. The line had a width of 0.1 centimeters and a length of 1 centimeter in the area to be adjacent to the conductive lead, and a width of 0.05 centimeters and a length of 1 centimeter in the area to be adjacent to the carbon electrode. Next, a detection working electrode was printed over the silver ink line with carbon ink (7101) obtained from DuPont Biosensor Group of Research Triangle Park, N.C. The detection working electrode had a width of 0.1 centimeters and a length of 0.3 centimeters. The connection between the carbon working electrode and the silver line was accomplished by overlapping the electrode and line.

An insulation layer and flow channel were then printed simultaneously onto the substrate using a UV-curable dielectric composition available from DuPont under the name "5018G." Printing was performed with a screen printer available from Affiliated Manufacturers, Inc. ("AMI-Presco") of North Branch, N.J. under the name "HC-53." The screen frame utilized had a size of 5×7 inches, a mesh size of 80×0.0037 to 400×0.0007, and a stencil angle of 22 to 45 degrees. The resulting insulation layer had a length of 4 centimeters and a width of 0.5 centimeters, and essentially covered the substrate area not otherwise covered by the electrodes, leads, or flow channels. The resulting flow channel had a length of 4 centimeters and a width of 0.1 centimeters. The height of the flow channel ranged from about 10 to about 150 micrometers, and was measured using a micrometer available from Mitutoyo America Corporation of Aurora, Ill.

B: The top strips: The top strips were also formed from a Mylar® plastic substrate available from DuPont. The substrate had a thickness ranging from 0.25 to 0.38 millimeters, a length of 4.5 centimeters, and a width of 1.3 centimeters. The substrate was initially printed with a silver ink line (5000) obtained from DuPont Biosensor Group of Research Triangle Park, N.C. The line had a width of 0.1 centimeters and a length of 1 centimeter in the area to be adjacent to the conductive lead, and a width of 0.05 centimeters and a length of 1 centimeter in the area to be adjacent to the silver/silver chloride electrode. Next, a counter/reference electrode was printed over the silver ink line with silver/silver chloride ink (5847) obtained from DuPont Biosensor Group of Research Triangle Park, N.C. The counter/reference electrode had a width of 0.2 centimeters and a length of 0.3 centimeters. An insulation layer was also printed onto the substrate using a UV-curable dielectric composition available from DuPont under the name "5018G", such as described above. The resulting insulation layer had a length of 3.4 centimeters and a width of 1.3 centimeters. Once formed, an area having a width of 0.95 centimeters and a length of 1.3 centimeters was cut from the top strip, such as shown in FIG. 2.

C. Curing and Drying: Once formed, the top and bottom strips were separately cured and dried. Specifically, the dielectric material used to form the strips was cured by placing the substrate under a solar simulator, which is available from Solar Light Co. of Philadelphia, Pa. under the name "LS 1000-4R-UV", for about 5 to 10 seconds. Thereafter, each strip was left at room temperature for 2 hours, and then heated at 37° C. for 2 hours. The temperature was then raised to 60° C. and dried an additional 2 hours. Thereafter, the temperature was again raised to between 120 to 140° C. for 20 minutes. Such stepwise drying helped achieve high uniformity of the electrode surface, while also removing residue solvents of the original ink formulations.

D. Electrode Surface Treatment: 0.5 microliters of LH-α-HRP monoclonal antibody conjugate (Fitzgerald Industries Int'l of Concord, Mass.) was drop coated onto the surface of the detection working electrode with an Eppendorf microliter pipette. The LH-α-HRP monoclonal antibody conjugate had a concentration of about 5 nanograms per milliliter in a mixture of 80% PBS buffer and 20% isopropanol, and had a pH of 7.4. The resulting electrode strip was then placed at room temperature and allowed to air dry. Thereafter, the coated working electrode was treated with 1 microliter of a protein stabilizing formulation (20 wt. % Stabilcoat® from SurModics, Inc. of Eden Prairie, Minn. and 0.05 wt. % Tween 20 in a PBS buffer, pH of 7.4). The incubation time was 15 minutes. After incubation, the remaining solution was removed by a wicking material, and the electrode strip was dried under an air stream. In addition, the entire detection area, including the working and counter/reference electrodes, was treated with about 100 microliters of a solution containing β-casein (1 wt. %), Tween 20 (0.05 wt. %), and PBS buffer (pH of 7.4), and dried.

E. Membrane Strips: Membrane strips of a nylon mesh (11 mesh size, commercially available from Millipore Corp. of Billerica, Mass.) were provided that had a length of 15 centimeters and a width ranging from 3.5 to 4.5 centimeters. Two glass fiber pads (sample and conjugate pads) were laminated to the bottom of the strip using tape. The conjugate pad was in direct contact with the membrane, and the sample pad was in direct contact with the conjugate pad. The conjugate pad was treated with 3 microliters of LH-α-HRP monoclonal antibody conjugate (5 micrograms per milliliter in PBS buffer)

and dried for 30 minutes. The LH-α-HRP monoclonal antibody conjugate was obtained from Fitzgerald Industries Int'l of Concord, Mass. The membrane strips were placed onto a sampling instrument commercially available from Kinematic Automation of Twain Harte, Calif. under the name "Matrix 2210 (Universal Laminator)." Thereafter, the strips were cut into individual strips having a width ranging from 1 to 10 millimeters using a strip cutter commercially available from Kinematic Automation under the name "Matrix 2360."

F. Lamination of Electrode Strips: To laminate the top and bottom electrode strips in a face-to-face relationship, double sided tape was first applied to the bottom strip. Specifically, the double sided tape was placed along both sides of the flow channel present on the bottom electrode strip. Thereafter, the membrane strip was placed over the flow channel and the surface of the working electrode. The top strip was then laminated in a face-to face relationship with the bottom strip, as shown in FIG. 3. After lamination, a cellulosic wicking pad (Millipore Co.) having a width of 0.95 centimeters and a length of 1.3 centimeters was placed into the pre-cut area on the top strip using tape.

Example 2

Laminated assay devices were formed in the manner described in Example 1. Thereafter, test samples were applied to the sample pad of the devices in an amount ranging from 10 to 100 microliters. The test sample contained an LH antigen in a concentration of 100 nanograms per milliliter in PBS buffer (pH of 7.42). The assay was allowed to develop until the wicking pad had absorbed almost all of the fluid from the test sample, which occurred in about 2 to about 15 minutes. A TMB substrate solution was then applied to the working electrode in an amount ranging from 10 to 30 microliters. Thereafter, a potential of about 0.1 to 0.3 volts was applied using a multi-channel VMP potentiostat commercially available from Perkin-Elmer, Inc. of Wellesley, Mass. The current was recorded after about 20 seconds, and effectively indicated the presence of the LH antigen.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An assay device for detecting the presence or quantity of an analyte residing in a test sample, the assay device comprising:
    a first substrate onto which is printed a detection working electrode capable of generating a measurable detection current and a calibration working electrode capable of generating a measurable calibration current, wherein the detection working electrode has a thickness of less than about 100 micrometers, the detection working electrode comprising an immobilized immunoreactive specific binding capture ligand for the analyte, the calibration working electrode being generally configured to not specifically bind the analyte;
    a second substrate onto which is printed an auxiliary electrode selected from the group consisting of a counter electrode, a reference electrode, and combinations thereof;
    a multi-channel potentiostat, the multi-channel potentiostat capable of receiving the detection current from the detection working electrode and the calibration current from the calibration working electrode; and
    wherein the first and second substrates are laminated together so that the auxiliary electrode is positioned adjacent to the detection working electrode and the calibration working electrode, wherein the detection current calibrated by the calibration current is proportional to the amount of the analyte within the test sample.

2. The assay device of claim 1, wherein the first substrate, the second substrate, or combinations thereof, are formed from an insulative material.

3. The assay device of claim 1, wherein both a counter electrode and a reference electrode are disposed on the second substrate.

4. The assay device of claim 3, wherein the detection working electrode further comprises a redox mediator.

5. The assay device of claim 1, wherein the assay device contains a redox label for directly or indirectly binding to the analyte.

6. The assay device of claim 5, wherein the redox label is used in conjunction with a particle modified with a specific binding member for the analyte.

7. The assay device of claim 1, wherein a sample channel is formed on the first substrate, the second substrate, or combinations thereof.

8. The assay device of claim 1, wherein the assay device comprises a porous membrane capable of being placed in fluid communication with the test sample.

9. The assay device of claim 1, wherein the specific binding capture ligand is selected from the group consisting of antigens, haptens, aptamers, antibodies, and complexes thereof.

10. The assay device of claim 4, wherein the redox mediator is selected from the group consisting of oxygen, ferrocene derivatives, quinones, ascorbic acids, redox polymers with metal complexes, glucose, redox hydrogel polymers, and organometallic complexes.

11. The assay device of claim 5, wherein the redox label is an enzyme selected from the group consisting of alkaline phosphatase, horseradish peroxidase, glucose oxidase, beta-galactosidase, urease, and combinations thereof.

12. The assay device of claim 1, wherein the auxiliary electrode contacts the first substrate only upon lamination of the first and second substrates.

13. The assay device of claim 1, wherein the specific binding capture ligand is immobilized on a surface of the detection working electrode.

14. The assay device of claim 1, wherein the detection working electrode is formed from an ink that is printed onto the first substrate.

15. The assay device of claim 1, wherein the auxiliary electrode is formed from an ink that is printed onto the second substrate.

16. The assay device of claim 1, wherein the detection working electrode has a thickness of less than about 50 micrometers.

17. The assay device of claim 1, wherein the detection working electrode has a thickness of less than about 20 micrometers.

18. The assay device of claim 1, wherein the detection working electrode has a thickness of less than about 5 micrometers.

* * * * *

UNITED STATES PATENT AND TRADEMARK OFFICE
CERTIFICATE OF CORRECTION

| | | |
|---|---|---|
| PATENT NO. | : 7,943,089 B2 | Page 1 of 1 |
| APPLICATION NO. | : 10/741434 | |
| DATED | : May 17, 2011 | |
| INVENTOR(S) | : Yang et al. | |

It is certified that error appears in the above-identified patent and that said Letters Patent is hereby corrected as shown below:

On the Title page

On page 3 References Cited, Column 2 under FOREIGN PATENT DOCUMENTS please add:

EP    0205698 A1    12/1986

Signed and Sealed this
Fourteenth Day of January, 2014

Michelle K. Lee
*Deputy Director of the United States Patent and Trademark Office*